US007132513B2

(12) United States Patent
Ouadi et al.

(10) Patent No.: US 7,132,513 B2
(45) Date of Patent: *Nov. 7, 2006

(54) BIFUNCTIONAL CHELATING AGENT

(75) Inventors: Ali Ouadi, Eggensteim (DE); Jean-François Gestin, Mauve sur Loire (FR); Christos Apostolidis, Heidelberg (DE)

(73) Assignees: European Community, Brussels (BE); INSERM Insitut National de la Santé et de la Recherche Médicale, Paris Cedex (FR)

( * ) Notice: Subject to any disclaimer, the term of this patent is extended or adjusted under 35 U.S.C. 154(b) by 337 days.

This patent is subject to a terminal disclaimer.

(21) Appl. No.: 10/204,905

(22) PCT Filed: Mar. 9, 2001

(86) PCT No.: PCT/EP01/02648

§ 371 (c)(1),
(2), (4) Date: Aug. 26, 2002

(87) PCT Pub. No.: WO01/68618

PCT Pub. Date: Sep. 20, 2001

(65) Prior Publication Data

US 2003/0027302 A1 Feb. 6, 2003

(30) Foreign Application Priority Data

Mar. 14, 2000 (LU) .......................................... 90544

(51) Int. Cl.
| C07K 16/00 | (2006.01) |
| C07D 259/00 | (2006.01) |
| G01N 33/534 | (2006.01) |
| C12N 9/96 | (2006.01) |
| A61K 51/00 | (2006.01) |

(52) U.S. Cl. .................... 530/391.5; 530/405; 530/409; 540/474; 436/545; 424/9.36; 424/9.364; 588/20; 588/318; 435/188

(58) Field of Classification Search ................ 540/474; 435/188; 530/391.5, 409, 405; 424/1.53, 424/9.364, 179.1, 9.36; 436/546, 545; 588/20, 588/318
See application file for complete search history.

(56) References Cited

U.S. PATENT DOCUMENTS 5,435,990 A * 7/1995 Cheng et al. .............. 424/1.53
6,696,551 B1 * 2/2004 Brechbiel et al. ............. 534/10

FOREIGN PATENT DOCUMENTS

| WO | WO 89/11475 | 11/1989 |
| WO | WO 95/20580 * | 8/1995 |
| WO | WO 00/59896 | 10/2000 |

OTHER PUBLICATIONS

Takenochi et al, "Preperation of bifunctional macrocyclic chelate ligands." Japanese Patent # 03197468, 1991, HCAPLUS Accession No. 1992:128980, Document No. 116:128980.*

Couturier, O., et al., "Validation of 213-Bi-alpha radioimmunotherapy for multiple myeloma". Clin. Cancer. Res., vol. 5, pp. 3165-3170, 1999.

Huneke, R. B., et al., "Effective alpha-particle-mediated Radioimmunotherapy of Murine Leukemia". Cancer Res., vol. 52, pp. 5818-5820, 1992.

Kozak, R. W., et al., "Bismuth-212-labeled anti-Tac monoclonal antibody: alpha-particle-emitting radionuclides as modalities for radioimmunotherapy". Proc. Natl. Acad. Sci. USA, vol. 83, pp. 474-478, 1986.

Macklis, R. M., et al., "Radioimmunotherapy with Alpha-Particle-Emitting Immunoconjugates". Science, vol. 240, pp. 1024-1026, 1988.

Kaspersen, F.M., et al., "Cytotoxicity of $^{213}$Bi- and $^{225}$Ac-immunoconjugates". Nucl. Med. Commun., vol. 16, pp. 468-476, 1995.

Kennel, S. J. "Radioimmunotherapy of micrometastases in lung with vascular targeted 213-Bi" British Journal of Cancer. vol. 80 (1/2), pp. 175-184, 1999.

(Previously Submitted) Kaspersen, F.M. "Cytotoxicity of 213 Bi- and 225 Ac-immunoconjugates" Nuclear Medicine Communications. vol. 16, pp. 468-476, 1995.

Davis, K.A. "Comparison of 225-Actinium Chelates: Tissue Distribution and Radiotoxicity" Nuclear Medicine & Biology, vol. 26, pp. 581-589, 1999.

Grote Gransey, M.H.B. "Conjugation, Immunoreactivity, and Immunogenicity of Calix[4 ]arenas; Model Study to Potential Calix[4 ]arene-Based Ac3+ Chelators" Bioconjugate Chem. vol. 10, pp. 613-623, 1999.

Deal, Kim A., et al., "Improved in Vivo Stability of Actinium-225 Macrocyclic Complexes". J. Med. Chem., 42, 2988-2992, (1999).

Takenochi, K., et al., "Preparation of bifunctional macrocyclic chelate ligands". Chemical Abstracts, vol. 116, No. 13, Abstract No. 128980, (Mar. 30, 1992).

* cited by examiner

Primary Examiner—Long V. Le
Assistant Examiner—Shafiqul Haq
(74) Attorney, Agent, or Firm—Nath & Associates; Gary M. Nath; Tanya E. Harkins

(57) ABSTRACT

The invention concerns a ligand comprising wherein n is an integer from 1 to 5, X represents —NO$_2$, —NH$_2$, —NCS, —NHCOCH$_2$-Z. NHCO—W—COCNHS, —NH-Q, —NHCS-Q, —NHCOCH$_2$-Q, or —NHCO(CH$_2$)$_L$m ?-Q where Q is an hapten chosen from the group consisting of steroids, enzymes, proteins, monoclonal antibodies, chimeric antibodies, or fragments thereof or any activated linker ready for coupling reaction, Y is CO$_2$H or PO$_3$H$_2$ W is —(CH$_2$)$_m$— m is an integer from 1 to 10. Z is chloride, bromide or iodine

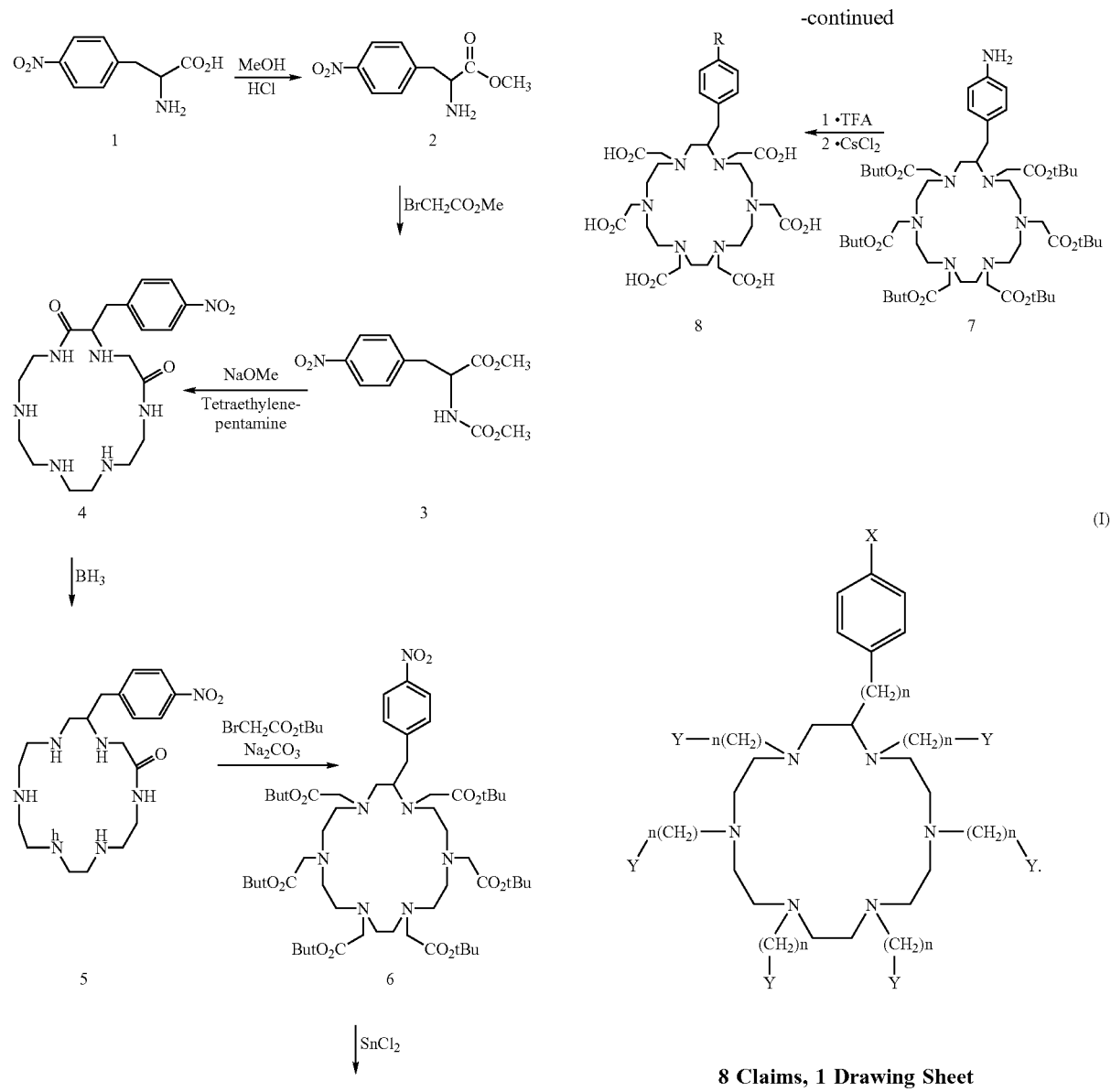
8 Claims, 1 Drawing Sheet

BIFUNCTIONAL CHELATING AGENT

TECHNICAL FIELD

The present invention relates to bifunctional chelating agents and more particular to bifunctional polyaza polycarboxylic or polyphosphonic macrocycles ligands a method of synthesis of these products and their uses.

BACKGROUND OF THE INVENTION

Alpha-emitting radionuclides are good potential candidates for radioimmunotherapy. $^{225}$Ac decays through a chain of 3 alpha emissions to $^{213}$Bi.

As described by Davis, I. A. et al in the article "Comparison of Actinium 225 Chelates: Tissue Distribution and Radiotoxicity" published in Nucl. Med. Biol., Vol. 26, pp 581–589, 1999; by Deal, K. A. et al. in the article "Improved in Vivo stability of Actinium-225 Macrocyclic Complexes" published in J. Med. Chem., Vol. 42, pp. 2988–2992, 1999 and by Grote Gansey, M. H. B. et al. in the article "Conjugation, Immunoreactivity, and Immunogenicity of Calix (4) arenes; Model Study to Potential Calix (4) arenes—Based Ac3+Chelators" published in Bioconj. Chem., Vol.10, pp 610–623, 1999, the stability of bifunctional chelating agent of actinides, lanthanides and bismuth is not satisfactory.

An object of the invention is to provide more effective bifunctional chelating agents for metals especially actinides and lanthanides and bismuth.

SUMMARY OF THE INVENTION

The present invention includes a ligand comprising:

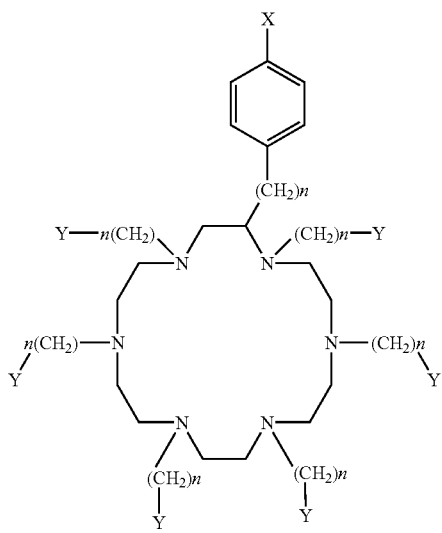

wherein
n is an integer from 1 to 5
X represents —NO$_2$, —NH$_2$, —NCS, —NHCOCH$_2$-Z, NHCO—W—COCNHS, —NH-Q, —NHCS-Q, —NHCOCH$_2$-Q, or —NHCO(CH$_2$)$_m$-Q where Q is an hapten chosen from the group consisting of steroids, enzymes, proteins, monoclonal antibodies, chimeric antibodies, or fragments thereof or any activated linker ready for coupling reaction, Y is CO$_2$H or PO$_3$H$_2$
W is —(CH$_2$)$_m$—
m is an integer from 1 to 10
Z is chloride, bromide or iodine.

If X represents —NH-Q, —NHCS-Q, —NHCOCH$_2$-Q, or —NHCO(CH$_2$)$_m$-Q where Q is a hapten chosen from the group consisting of steroids, enzymes, proteins, monoclonal antibodies, chimeric antibodies, humanised antibodies or fragments thereof, the resulting ligand is also called a ligand-hapten conjugate.

The invention also includes according to a preferred embodiment, a metal chelate of the ligand as described above wherein the metal is chosen from the group consisting of the lanthanides and the actinides. The metal is preferably actinium and most preferably actinium-225 ($^{225}$Ac).

The invention also includes according to a preferred embodiment, a metal chelate of the ligand as described above wherein the metal is preferably bismuth and most preferably bismuth-213 ($^{213}$Bi).

The present invention also includes a process for the preparation of said ligand, said process comprising a bimolecular cyclization between an iminodiester and a polyamine by the action of a molar equivalent of sodium methoxide.

The present invention also includes the method of using the metal chelates of the ligand-hapten conjugate possessing a linking group wherein the chelate as a therapeutic or diagnostic agent.

Specifically, such ligands are useful for radiolabeling proteins with radioactive metals, and can consequently be utilised with respect to radioimmunoimaging and/or radioimmunotherapy. The present the ligand-hapten conjugates firmly link metals especially actinides, lanthanides and bismuth to proteins, minimise metal release and permit high selective delivery of metals to targeted sites in vivo. This is especially true for the actinium and bismuth complexation metal chelate protein conjugates.

Immunotherapy with radiolabelled antibodies allows fairly specific targeting of certain cancers (see f.ex. Couturier, O. et al. "Validation of 213-Bi-alpha radioimmunotherapy for multiple myeloma" in Clin. Cancer. Res., Vol. 5, pp. 3165–3170, 1999; Huneke, R. B., et al. in "Effective alpha-particle-mediated radioimmunotherapy of murine leukemia" in Cancer Res., Vol. 52, pp. 5818–5820, 1992; Kennel, S. J. et al. "Radioimmunotherapy of micrometastases in lung with vascular targeted 213Bi" in Br. J . Cancer, Vol. 80, pp. 175–184, 1999; Kozak, R. W. et al. "Bismuth-212-labeled anti-Tac monoclonal antibody alpha-particle-emitting radionuclides as modalities for radioimmunotherapy" in Proc. Natl. Acad. Sci. USA, Vol. 83, pp. 474–478, 1986 or Macklis, R. M. et al. "Radioimmunotherapy with alpha-particle-emitting immunoconjugates" in Science, Vol. 240, pp. 1024–1026, 1988.

This technique is based on the use of radionuclides associated to antibodies or peptides that are specific of antigens expressed on the tumour cells. In order to bind a radionuclide to a vector it is necessary to use bifunctional chelating agents (BCA) that have two specific sites. One site is to be coupled to the vector and the other has to form very stable complexes with the radionuclide to be used.

$^{225}$Ac and $^{213}$Bi are good candidates for such applications as described by Kaspersen, F. M. et al. "Cytotoxicity of 213Bi- and 225Ac-immunoconjugates" in Nucl. Med. Commun., Vol. 16, pp. 468–476, 1995. The very short range (<100 μm) of α-particles and the high energy transfer allows efficient destruction of tumor cells whereas normal cells are relatively spared.

Chelators that can hold radioactive metals with high stability under physiological conditions are essential to avoid excessive radiation damage to non-target cells.

Furthermore, these bifunctional chelating agents allow different applications; it can be used to bind $^{225}$Ac or other actinides and lanthanides or $^{213}$Bi to any biological or non-biological structures for any applications.

These chelating agents can be used non-associated to a vector as a detoxication chelating agent or using the natural tropism of the complex.

This chelating agent can also be used grafted on a chromatographic column in order to purify or concentrate any solutions containing $^{225}$Ac or other actinides, lanthanides or $^{213}$Bi.

The complexation properties of our product with $^{225}$Ac or other actinides or lanthanides show that this chelating agent may also be useful as a good extractant in the process of separation of minor actinides and lanthanides in nuclear waste or to separate specific groups of metals in high level waste.

BRIEF DESCRIPTION OF THE DRAWINGS

Embodiments of the present invention are described by way of example and with reference to the accompanying drawing wherein.

An access route that allows the synthesis of a bifunctional macrocycle-chelating agent is described in FIG. 1.

DETAILED DESCRIPTION

Figure 1:
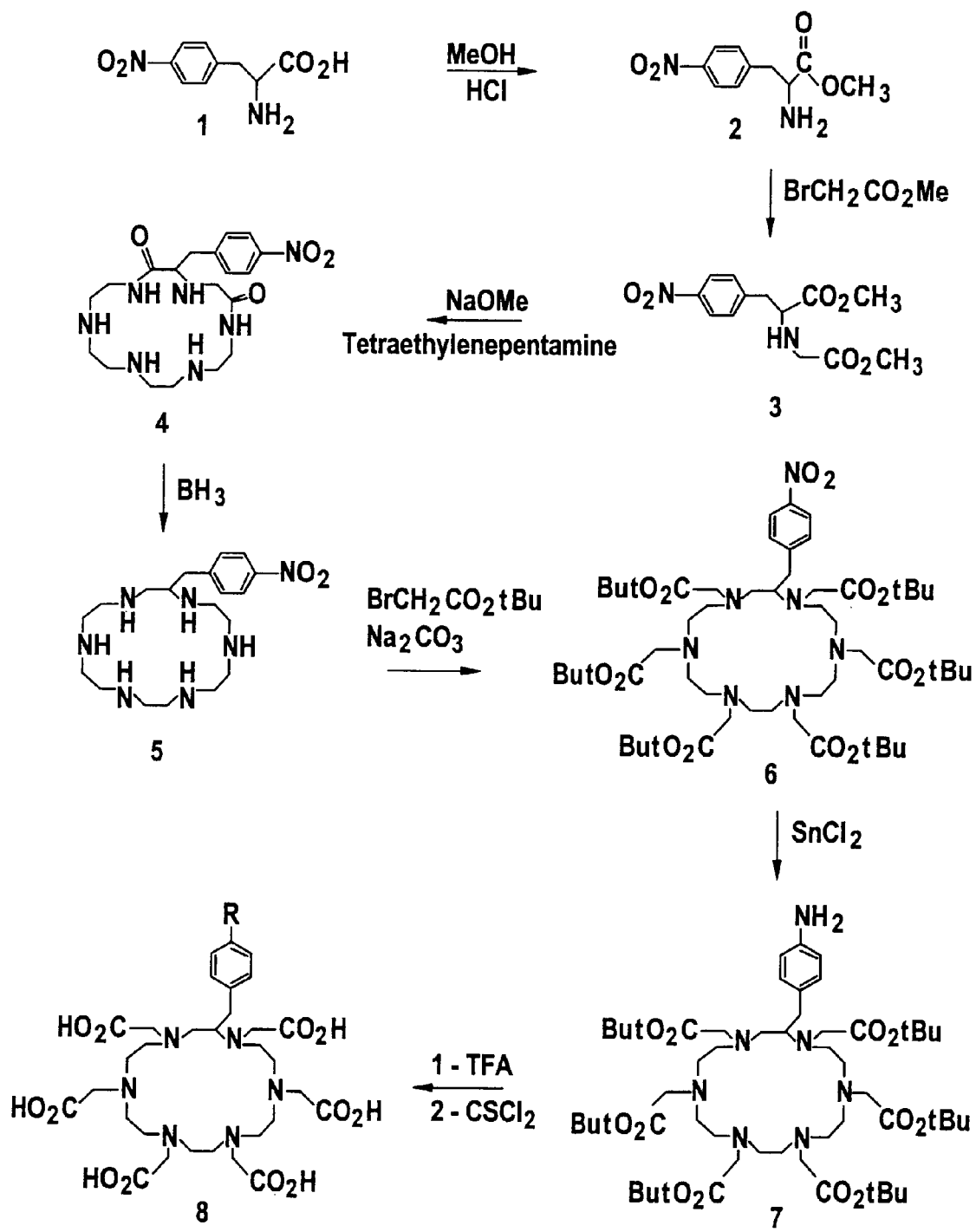
FIG. 1. represents a scheme for the preparation of a substituted 1,4,7,10,13,16-hexa(2-carboxymethyl)-hexaazacyclooctadecane ligand (HEHA).

Different non-functionalised chelating agents (commercially available or readily synthesised in the laboratory) bearing aminocarboxylate groups (EDTA, DTPA, DOTA, PEPA, and HEHA) or aminophosphonate groups (EDTMP) were tested for their complexation properties with $^{225}$Ac and $^{213}$Bi. It was found that HEHA compound (1,4,7,10,13,16-hexacarboxylmethyl-1,4,7,10,13,16-hexaazacyclooctadecane) appeared to be the best candidate for $^{225}$Ac complexation. This result is in balance in regard of previous studies. Polyaza polycarboxylic macrocycles are known to form thermodynamically stable complexes with large metal ions such as actinides and lanthanides.

It was also found that HEHA appeared to be a good chelating agent of $^{213}$Bi.

Therefore, after selection of the suitable candidate, a method of the synthesis of the C-functionalised analogue was set up. To achieve that, the 2-(4-isothiocyanatobenzyl)-1,4,7,10,13,16-hexakis(2-carboxymethyl)-hexaazacyclooctadecane compound which is functionalised at C-2 on the cycle by either an isothiocyanate termination for future covalent attachment to biomolecules or any activated linker ready for coupling reaction was prepared.

Macrocyclic polyamines, the key precursors to macrocyclic bifunctional chelating agents are synthesised by different way: the Richman-Atkins cyclization of deprotonated tosylamides with tosylates in aprotic solvents, the <<crab-like<< (cyclization of a bis (α-chloroamide) with amines, the Tabushi cyclization (aminolyse of malonates with polyamines) or via peptide synthesis and intramolecular tosylamide ring closure.

However, the efforts to prepare the 2-(4-isothiocyanatobenzyl)-1,4,7,10,13,16-hexakis(2-carboxymethyl)-hexaazacyclooctadecane with these classical methods failed.

A different synthetic route to the bifunctional macrocycles via aminolyse of an iminodiester with a polyamine of in the presence of NaOMe was developed. The reaction between N-methoxycarbonylmethyl-p-nitrophenylalanine methyl ester and tetraethylenepentamine upon refluxing in methanol for several days in the absence of sodium methoxide were not concluent.

An improved procedure for the bimolecular cyclization between an iminodiester and a polyamine by the action of a molar equivalent of sodium methoxide is described in more detail. Yield of 50% was obtained to prepare the bifunctional dioxoaza macrocycle without resorting to high dilution. This surprising methodology which was developed is simple and convenient and allows preparation of functionnalised macrocyclic polyamines of varying ring size.

Referring now to the FIGURE, the synthesis of 2-(4-isothiocyanatobenzyl)-1,4,7,10,13,16-hexa(2-carboxymethyl)-hexaazacyclooctadecane is described in more detail.

The commercial product, 4-nitrophenylalanine (1) was used as starting material.

Treatment of (1) with HCl gas in methanol led to the 4-nitrophenylalanine methyl ester hydrochloride (2). Compound (2) was monoalkylated by methylbromoacetate in the presence of triethylamine to give diester N-((methoxycarbonyl)methyl)-4-nitrophenylalanine methyl ester (3). Treatment of (3) with tetraethylenepentamine in the presence of sodium methanolate in refluxing methanol resulted in macrocyclisation to give the cyclic diamide 3-(4-nitrobenzyl)-2,6-dioxo-1,4,7,10,13,16-hexaazacyclooctadecane (4). Reduction with BH$_3$ afforded after treatment with HCl gas and purification by anion-exchange chromatography the 2-(4-nitrobenzyl)-1,4,7,10,13,16-hexaazacyclooctadecane (5). Treatment of (5) with ter-butyl bromoacetate in the presence of sodium carbonate gave the hexaester 2-(4-nitrobenzyl)-1,4,7,10,13,16-hexakis-(tert-butoxycarbonylmethyl)-1,4,7,10,13,16-hexaazacyclooctadecane (6). The nitrobenzyl function was selectively reduced by using tin chloride in ethanol to obtain the aminobenzyl compound 2-(4-aminobenzyl)-1,4,7,10,13,16-hexakis(tert-butoxycarbonylmethyl)-1,4,7,10,13,16-hexaazacyclooctadecane (7). Cleavage of the ester groups with trifluoroacetic acid followed by purification on ion exchange chromatography column and treatment with thiophosgene gave the final compound 2-(4-isothiocyanatobenzyl)-1,4,7,10,13,16-hexa (2-carboxymethyl)-hexaazacyclooctadecane (8) (AOI032).

An alternative to isothiocyanato coupling function can be used by introducing different activated linkers. It is also possible to replace aminocarboxylate groups by aminophosphonate groups to complex the metal to be used.

In conclusion, different non-functionalised chelating agents bearing aminocarboxylate or aminophosphonate groups were tested for their complexation properties with $^{225}$Ac and $^{213}$Bi. After selection of the best candidate, the C-functionalised analogue was synthesised.

EXAMPLE

4-Nitrophenylalanine methyl ester hydrochloride (2)

4-Nitrophenylalanine (1) (24 mmol) was treated with methanol (100 ml) saturated with HCl (g) and left to stir at room temperature for 18 hours. The solution was concentrated by evaporating to ⅓ of original volume and the precipitate was collected and dried under vacuum for 18 hours. The yield was 85%.

NMR $^1$H (250 MHz, D2O): δ 8.2 (d, 2H), 7.53 (d, 2H), 4.55 (t, 1H), 3.84 (s, 3H), 3.43 (m, 2H).

N-((Methoxycarbonyl)methyl)-4-Nitrophenylalanine methyl ester (3)

Triethylamine (22 mmol) was added to a suspension of 4-Nitrophenylalanine methyl ester hydrochloride (2) (21 mmol) in THF (50 ml). The mixture was stirred at room temperature for one hour, the triethylamine hydrochloride was filtered off, and the filtrate concentrated to yellow oil. The oil was dissolved in dry THF (50 ml) and to this solution was added triethylamine (60 mmol) and methylbromoacetate (60 mmol), the solution was stirred at room temperature under nitrogen atmosphere for 3 hours, after which the precipitate was filtered off and the filtrate concentrated on vacuum. The residue was dissolved in ethylacetate, washed with $H_2O$, dried ($MgSO_4$) and concentrated on vacuum to give yellow oil. The yield was 92%.

MS (M+1): 297

NMR $^1H$ (250 MHz, CHCL3): δ 8.2 (d, 2H), 7.53 (d, 2H), 3.7 (m, 7H), 3.3 (m, 2H), 3.1 (m, 2H).

3-(4-nitrobenzyl)-2,6-dioxo-1,4,7,10,13,16-hexaazacyclooctadecane (4)

Sodium (20 mmol) was dissolved in dry methanol (100 ml) at room temperature under nitrogen atmosphere and to this solution was added tetraethylenepentamine (18 mmol) and N-((Methoxycarbonyl)methyl)-4-Nitrophenylaianine methyl ester (3) (18 mmol). This solution was refluxed for 72 hours after which the solvent was removed and the residue was purified on silica gel chromatography with chloroformelmethanol/$NH_3$ (aq) (75:20:5), affording a yellow powder. The yield was 50%.

MS (M+1): 422

IR (Kr, $cm^{-1}$); 3287 (NH); 3287–2842 (Ar—C—H); 1656 (C=O); 1517 and 1345 ($NO_2$)

NMR $^1H$ (250 MHz, $CDCL_3$): δ 8.17 (d, 2H), 7.57 (s, NH amide), 7.40 (d, 2H), 7.27 (s, NH amide), 3.14–3.48 (m, 9H), 2.6–2.9 (m, 11H).

NMR $^{13}C$ ($CDCl_3$): CO: 175, 145, 130, 123, 55, 52, 40

2-(4-nitrobenzyl)-1,4,7,10,13,16-hexaazacyclooctadecane (5)

A solution of $BH_3$ in THF (100 mmol) was added dropwise to a stirred suspension of 3-(4-nitrobenzyl)-2,6-dioxo-1,4,7,10,13,16-hexaazacyclooctadecane (4) (10 mmol) in THF (50 ml) at 0° C. under nitrogen atmosphere. The solution was heated at reflux for 36 hours. Methanol was added slowly to the solution at 0° C. after which the solvent was removed and the residue was dissolved in methanol (50 ml); the resulting mixture was cooled at 0° C. and gaseous HCl was bubbled through the solution and then the mixture was refluxed for 12 hours. The resulting precipitate was collected washed with ether to give a white powder. The solid was dissolved in water and was loaded on a column of DOWEX 1X-8 anion-exchange resin ($OH^-$ form). The column was eluted with water; alkaline fractions were collected, and the water was removed under vacuum to give pale yellow oil. The yield was 55%.

MS (M+1): 394

IR (Kr, $cm^{-1}$): 3428 (NH); 2961–2759 (Ar—C—H), 1518 and 1349 ($NO_2$)

The I.R. spectrum showed no band at 1656 $cm^{-1}$ for the C=O group.

NMR $^1H$ (250 MHz, $CDCL_3$): δ8.06 (d, 2H), 7.27 (d, 2H), 2.3–2.9 (m, 25H)

2-(4-nitrobenzyl)-1,4,7,10,13,16-hexakis(tert-butoxycarbonylmethyl) -1,4,7,10,13,16-hexaazacyclooctadecane (6)

To a solution of 2-(4-nitrobenzyl)-1,4,7,10,13,16-hexaazacyclooctadecane (5) (10 mmol) in DMF (50 ml) at room temperature under a nitrogen atmosphere was added anhydrous sodium carbonate (0.11 mol) and a solution of tert-butyl bromoacetate (62 mmol) in DMF (20 ml). The mixture was heated at 60° C. for 18 hours after which the solvent was removed and the residue was dissolved in chloroform washed with brine, dried ($MgSO_4$) and concentrated on vacuum to give yellow oil. The yield was 82%.

MS (M+1): 1078

2-(4-aminobenzyl)-1,4,7,10,13,16-hexakis(tert-butoxvcarbonvlmethyl) -1,4,7,10,13,16-hexaazacyclooctadecane (7)

To a solution of 2-(4-nitrobenzyl)-1,4,7,10,13,16-hexakis(tert-butoxycarbonylmethyl) -1,4,7,10,13,16-hexaazacycloocta (6) (15 mmol) in ethanol (50 ml) at room temperature under a nitrogen atmosphere was added $SnCl_2$ (0.125 mol). The mixture was refluxed for 12 hours after which the solvent was removed and the compound thus obtained was dissolved in water; the solution was brought to pH 8 with 2M NaOH. The resulting precipitate was removed off and the filtrate concentrated on vacuum; the residue was dissolved in acetonitrile and passed over Celite. The filtrate was evaporated on vacuum to give yellow oil. The yield was 62%.

MS (M+1): 1048

2-(4-isothiocyanatobenzyl)-1,4,7,10,13,16-hexakis (2-carboxymethyl) -1,4,7,10,13,16-hexaazacyclooctadecane (8)

2-(4-aminobenzyl)-1,4,7,10,13,16-hexakis(tert-butoxycarbonylmethyl) -1,4,7,10,13,16-hexaazacyclooctadecane (7) (10 mmol) was treated with TFA (0,1 mol) 6 hours at room temperature under nitrogen atmosphere after which the solvent was removed. The compound thus obtained was dissolved in water and loaded on a column of DOWEX 50WX8-200 ($H^+$ form).

The column was eluted consecutively with 0.5 M HCl and with water until the eluant was neutral and finally with 0.5 M aqueous ammonia solution. Alkaline fractions were collected, and the water was removed on vacuum to give 2-(4-aminobenzyl)-1,4,7,10,13,16-hexakis(2-carboxymethyl) -1,4,7,10,13,16-hexaazacyclooctadecane as pale yellow oil.

MS (M+1): 712

NMR $^1H$ (250 MHz, $D_2O$): δ 7.08 (d, 2H), 6.80 (d, 2H), 2.5–4.0 (m, 37H)

The compound thus obtained was dissolved in water and the pH was adjusted to 9.0 with $NaHCO_3$. To this solution was added at room temperature under nitrogen atmosphere thiophosgene in $CHCl_3$ (10 ml), the mixture was stirred for 2 hours. The organic layer was removed and the water was evaporated on vacuum to give the final product (8) (AO1032).

The yield was 65%.

MS (M+1): 754

The I.R. spectrum showed a strong band at 2100 cm for the aryl SCN group.

While a preferred embodiment of the present invention has been described, it will apparent to those skilled in the art that many changes and modifications may be made without departing from the invention in its broader aspects. The appended claims are therefore intended to cover all such changes and modifications as fall within the true spirit and scope of the invention.

The invention claimed is:

1. A ligand comprising

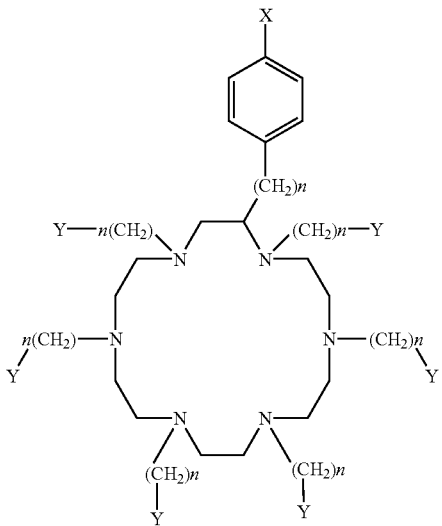

wherein n is an integer from 2 to 5

X represents —NHCO—(CH2)m-COCNHS, —NH-Q, —NHCS-Q, —NHCOCH$_2$-Q, or —NHCO(CH$_2$)$_m$-Q and where Q is an hapten chosen from the group consisting of steroids, enzymes, proteins, monoclonal antibodies, chimeric antibodies; and m is an integer from 1 to 10.

2. A metal chelate of the ligand of claim 1, wherein the metal is chosen from the group consisting of the lanthanides and the actinides.

3. A metal chelate of the ligand of claim 2, wherein the metal is actinium.

4. A metal chelate of the ligand of claim 3, wherein the metal is actinium-225 ($^{225}$Ac).

5. A metal chelate of the ligand of claim 1, wherein the metal is bismuth.

6. A metal chelate of the ligand of claim 5, wherein the metal is bismuth-213.

7. A metal chelate of a ligand comprising

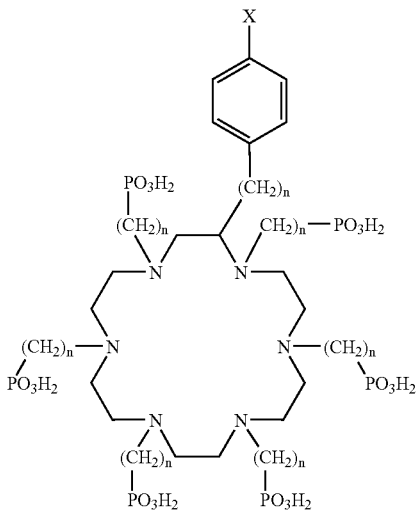

wherein n is an integer from 2 to 5

X represents —NHCO—(CH2)m-COCNHS —NH-Q, —NHCS-Q, —NHCOCH$_2$-Q, or —NHCO(CH$_2$)$_m$-Q and where Q is an hapten chosen from the group consisting of steroids, enzymes; proteins, monoclonal antibodies, chimeric antibodies m is an integer from 1 to 10 wherein the metal is actinium, and wherein said ligand is prepared by a process comprising a bimolecular cyclization between an iminodiester and a polyamine by the action of a molar equivalent of sodium methoxide.

8. A metal chelate of the ligand of claim 7, wherein the metal is actinium-225 ($^{225}$Ac).

* * * * *

UNITED STATES PATENT AND TRADEMARK OFFICE
CERTIFICATE OF CORRECTION

PATENT NO. : 7,132,513 B2  
APPLICATION NO. : 10/204905  
DATED : November 7, 2006  
INVENTOR(S) : Ouadi et al.

Page 1 of 2

It is certified that error appears in the above-identified patent and that said Letters Patent is hereby corrected as shown below:

Claim 1, Column 7, Line 7,
Please delete

"
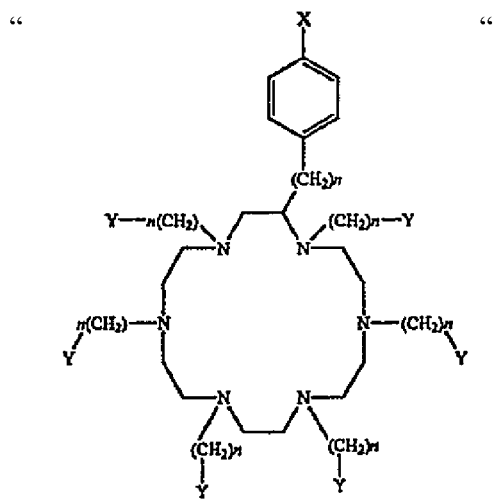
"

and replace with

--
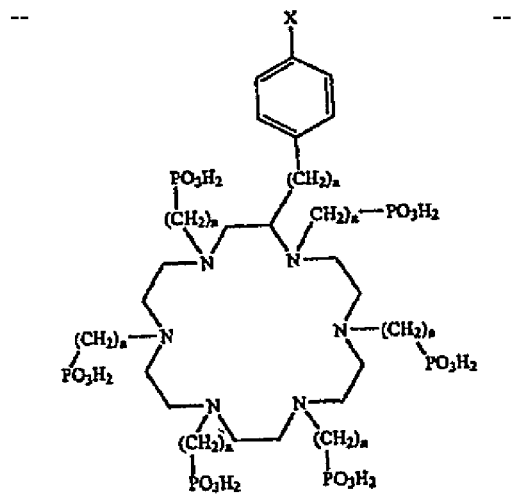
--

UNITED STATES PATENT AND TRADEMARK OFFICE
CERTIFICATE OF CORRECTION

PATENT NO. : 7,132,513 B2
APPLICATION NO. : 10/204905
DATED : November 7, 2006
INVENTOR(S) : Ouadi et al.

It is certified that error appears in the above-identified patent and that said Letters Patent is hereby corrected as shown below:

Claim 1, Column 7, Lines 37 and 38,
Please delete "monoclonal antibodies, chimeric antibodies;" and
replace with -- monoclonal antibodies, and chimeric antibodies; --

Claim 7, Column 8, Lines 34 and 35,
Please delete "monoclonal antibodies, chimeric antibodies" and
replace with -- monoclonal antibodies, and chimeric antibodies; and --

Claim 7, Column 8, Line 34,
Please delete " enzymes; proteins, " and
replace with -- enzymes, proteins, --

Signed and Sealed this

First Day of May, 2007

JON W. DUDAS
*Director of the United States Patent and Trademark Office*